United States Patent [19]

Mosby

[11] 3,936,481
[45] Feb. 3, 1976

[54] HYDRAZONO-1,3,2-DITHIARSETANES, -STANNETANES AND -STIBITANES

[75] Inventor: William Lindsay Mosby, North Plainfield, N.J.

[73] Assignee: American Cyanamid Company, Stamford, Conn.

[22] Filed: Nov. 1, 1973

[21] Appl. No.: 412,000

[52] U.S. Cl. .............. 260/429.7; 71/97; 260/440; 260/446; 260/999
[51] Int. Cl. ............................................. C07f 7/22
[58] Field of Search ................ 260/429.7, 440, 446

[56] References Cited
UNITED STATES PATENTS

| | | | |
|---|---|---|---|
| 3,316,284 | 4/1967 | Stamm et al. | 260/429.7 |
| 3,365,478 | 1/1968 | Mosby | 260/429.7 |
| 3,429,905 | 2/1969 | Mosby | 260/429.7 |

Primary Examiner—H. Sneed
Attorney, Agent, or Firm—Charles J. Fickey

[57] ABSTRACT

New hydrazono-1,3,2-dithiarsetanes, -stannetanes and -stibitanes are provided which have biocidal activity.

7 Claims, No Drawings

HYDRAZONO-1,3,2-DITHIARSETANES, -STANNETANES AND -STIBITANES

Generally stated, the subject matter of the present invention relates to hydrazono-1,3,2-dithiarsetanes, -stannetanes and stibitanes.

THE INVENTION

The present invention, in accordance with its purpose as embodied and broadly described, provides hydrazono-1,3,2-dithiarsetanes, -stannetanes and stibitanes having the following formula:

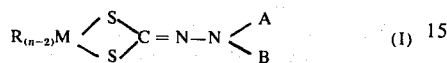

wherein M is a polyvalent metal selected from the group consisting of antimony, arsenic and tin; R is a monovalent hydrocarbyl radical selected from the group consisting of lower alkyl (including cycloalkyl of 4–6 carbons), mono or bicyclic aromatic (e.g., phenyl and naphthyl as well as lower alkyl substituted analogs), and monocyclic aralkyl; n is an integer of 3 or 4; A is lower alkyl, —CO-aryl or —SO$_2$-aryl; B is hydrogen or lower alkyl; or A and B taken together are polymethylene of 4 to 5 carbons; and aryl is monocyclic.

The compounds of this invention exhibit biocidal properties. Herbicidal activity toward wheat, radish, cucumber and corn; fungicidal activity toward *Aspergillus niger* and *Stemphylium Sarcinaeforme*; nematocidal activity toward *Turbatrix aceti*; and insecticidal activity were shown. Accordingly, the compounds can be used agriculturally in conventional formulations as fungicides, herbicides, nematocides and insecticides.

The compounds of this invention can be prepared by reacting an organo-metalic dihalide of Formula II with a dialkali metal salt of a substituted dithiocarbazic acid of Formula III as in the following equation:

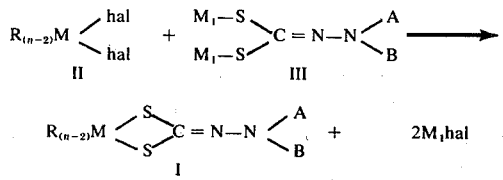

wherein R, M, A, B and *n* are as defined above, "hal" is halogen of atomic number above 9, and M$_1$ is an alkali metal such as sodium or potassium. The reaction can be carried out by contacting approximately equimolar amounts of the dihalide and dithiolate in a suitable reaction medium.

Suitable inert reaction media include dibutylether, acetonitrile, dimethylformamide, "Diglyme", dimethyylacetamide, dimethyl sulfoxide, etc.

When the two reactants are contacted, some heat is usually evolved. Therefore, it is usually advantageous to combine the reactants at room temperature. Under certain conditions, it may be necessary to provide a cooling means to remove the heat of reaction. In a few cases, it may be necessary to apply heat to promote the completion of the reaction. Temperatures between room temperature and the boiling point of the reaction medium may be used. The reactions are rapid and usually require only a short time for completion.

The reaction products may be isolated by any convenient means. It is advantageous to add water, when a watermiscible reaction medium has been used, whereupon the product precipitates, if it is not already precipitated.

Five types of organo-metalic dihalides may be used in the preparation of the compounds of this invention. They are shown in the following general formulae:

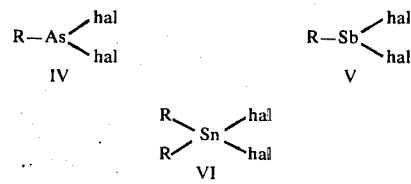

Accordingly, three main types of compounds of Formula I can be obtained by varying the particular dihalide which is reacted with the dithiolate. The types are shown in the following formulae:

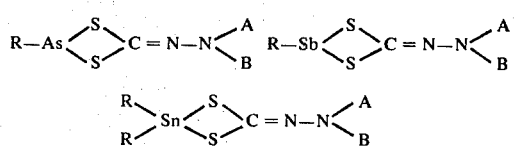

Representative organo dihalides of trivalent arsenic in Formula IV are alkyl- and aryl-dihaloarsines, such as methyldichloroarsine, methyldiiodoarsine, methyldichloroarsine, ethyldibromoarsine, amyldibromoarsine, heptyldichloroarsine, trifluoromethyldibromoarsine, ethoxyethyldichloroarsine, phenyldibromoarsine, phenyldiiodoarsine, phenyldichloroarsine, o-tolyldichloroarsine, 2-naphthyldichloroarsine, p-chlorophenyldichloroarsine, m-nitrophenyldichloroarsine, 2,5-dimethylphenyldichloroarsine, 4acetamidophenyldichloroarsine, 4acetamidophenyldichloroansine, benzyldichloroarsine, etc.

Representative organo dihalides of trivalent antimony in Formula V are alkyl- and aryl-dihalostibines, such as methyldichlorostibine, ethyldichlorostibine, phenyldiiodostibine, p-nitrophenyldichlorostibine, p-tolyldichlorostibine, p-ethylphenyldichlorostibine, 2-naphthyldichlorostibine, etc.

Representative organo-tin dihalides of Formula VIII are dialkyl- and diaryl-dihalo-tin compounds such as dimethyldichlorotin, diethyldibromotin, dibutyldibromotin, diamyldichlorotin, dioctyldichlorotin, didecyldichlorotin, butylpropyldichlorotin, diphenyldiiodotin, di-p-tolyldichlorotin, bis-(p-methoxyphenyl)dichlorotin, dibenzyldiiodotin, dicyclohexyldichlorotin, etc.

As indicated above; three classes of compounds of Formula III may be used in reaction 1. These are shown by Formulas VII, VIII and IX.

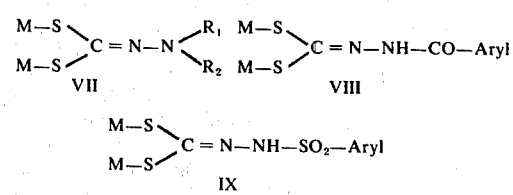

Examples of VII include the dialkali metal salts of 3,3-dimethyldithiocarbazic acid, 3,3-tetramethylenedithiocarbazic acid, etc.

Examples of VIII include the dialkali metal salts of 3-benzoyldithiocarbazic acid, etc.

Examples of IX include the dialkali metal salts of 3-phenylsulfonyldithiocarbazic acid, etc.

The following examples are provided for illustrative purposes and may include particular features of the invention. However, the examples should not be construed as limiting the invention, many variations of which are possible without departing from the spirit or scope thereof.

EXAMPLE I

4-Dimethylhydrazono-2,2-diphenyl-1,3,2-dithiastannetane

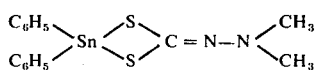

A solution of 5.3 g. of dipotassium 3,3-dimethyldithiocarbazate in 30 ml. of the dimethylformamide is added to a cool solution of 8.6 g. of diphenyldichlorotin in 50 ml. of dimethylformamide. After about 1 hour at ambient temperature, 200 ml. of water is added and the white granular precipitate is separated by filtration, washed with water and dried. The product melts at about 72.5°–74.5°C.

Following the same procedure except for the replacement of the diphenyldichlorotin by dibutyldichlorotin, the compound 4-dimethylhydrazone-2,2-butyl-1,3,2-dithiastannetane is obtained.

EXAMPLE II

4-Benzoylhydrazono-2,2-diphenyl-1,3,2-dithiastannetane

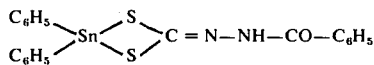

A solution of 6.9 g. of diphenyldichlorotin in 50 ml. of dimethylformamide is added to a cool solution of dipotassium 3-benzoyldithiocarbazate in 30 ml. of dimethylformamide. Water (about 400 ml.) is added to the yellow solution. The precipitate is separated and washed with water and methanol. The resulting yellow gum is recrystallized from benzene and ligroin to obtain a white solid.

Following the same procedure except for the replacement of the dipotassium 3-benzoyldithiocarbazate by dipotassium 3-phenylsulfonyldithiocarbazate, the compound 4-phenylsulfonylhydrazono-2,2-diphenyl-1,3,2-dithiastannetane is obtained.

EXAMPLE III 4-(Tetramethylenehydrazono)-2,2-diphenyl-1,3,2-dithiastannetane

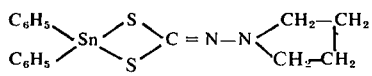

A solution of about 2.4 g. of dipotassium 3,3-tetramethylenedithiocarbazate in 6 ml. of dimethylformamide is added to a cool solution of 1.72 g. of diphenyldichlorotin in 10 ml. of dimethylformamide. The yellow solution is diluted with water and the precipitate is separated and dried. The melting point of the product is in the range of 100°–105°C.

EXAMPLE IV

4-Dimethylhydrazono-2-phenyl-1,3,2-dithiarsetane

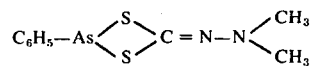

Phenyldiiodoarsine (4.06 g.) is slowly added to a cooled solution of about 3.8 g. of dipotassium 3,3-dimethyldithiocarbazate in 3 ml. of dimethylformamide. The reaction mixture is diluted with water and the white precipitate is separated and washed with water. The product melts at about 117.5°–119.5°C.

EXAMPLE V

4-Benzoylhydrazone-2-phenyl-1,3,2-dithiarsetane

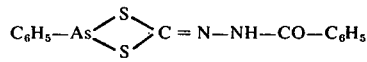

Phenyldiiodarsine (6.09 g.) is slowly added to a cool slurry of 4.32 g. of dipotassium 3-benzoyldithiocarbazate in 3 ml. of dimethylformamide. The yellow reaction mixture is diluted with about 200 ml. of water and the precipitate is separated and washed with water and ligroin. The precipitate is recrystallized from ethyl acetate with addition of ligroin and then from dimethylformamide with addition of water. The white product melts with the decomposition in the range of 90°–100°C.

I claim:
1. A compound of the formula:

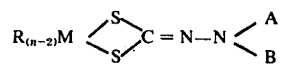

wherein M is a polyvalent metal selected from the group consisting of antimony, arsenic and tin; R is a monovalent hydrocarbyl radical selected from the group consisting of lower alkyl, mono or bicyclic aromatic, and monocyclic aralkyl; n is an integer of 3 when M is arsenic or antimony and 4 when M is tin; A is lower alkyl, —CO—aryl or —SO$_2$—aryl; B is hydrogen or lower alkyl; and aryl is monocyclic.

2. The compound according to claim 1, 4-dimethylhydrazono-2,2-diphenyl-1,3,2-dithiastannetane.

3. The compound according to claim 1, 4-benzoylhydrazono-2,2-diphenyl-1,3,2-dithiastannetane.

4. The compound according to claim 1, 4-dimethylhydrazono-2-phenyl-1,3,2-dithiarsetane.

5. The compound according to claim 1, 4-benzoylhydrazono-2-phenyl-1,3,2-dithiarsetane.

6. The compound according to claim 1 wherein R is a cycloalkyl of 4 to 6 carbon atoms.

7. The compound according to claim 1 wherein R is a mono or bicyclic aromatic and is a member selected from the group consisting of phenyl, naphthyl and lower alkyl substituted analogs thereof.

* * * * *